United States Patent [19]

Cleary

[11] Patent Number: 4,472,585

[45] Date of Patent: Sep. 18, 1984

[54] EXTRACTION OF N-METHYLPYRROLIDONE-2

[75] Inventor: James W. Cleary, Bartlesville, Okla.

[73] Assignee: Phillips Petroleum Company, Bartlesville, Okla.

[21] Appl. No.: 385,755

[22] Filed: Jun. 7, 1982

[51] Int. Cl.³ .......................................... C07D 207/267
[52] U.S. Cl. ..................................... 548/555; 260/705
[58] Field of Search .......................................... 548/555

[56] References Cited

U.S. PATENT DOCUMENTS

| | | | |
|---|---|---|---|
| 2,802,777 | 8/1957 | Lohr | 548/555 |
| 2,939,869 | 6/1960 | Carlson | 548/555 |
| 2,944,944 | 7/1960 | Clayton | 548/555 |
| 4,013,549 | 3/1977 | Bushnell | 208/323 |

FOREIGN PATENT DOCUMENTS 46-32263  9/1971  Japan .................................. 548/555

*Primary Examiner*—Paul M. Coughlan, Jr.
*Assistant Examiner*—D. B. Springer

[57] ABSTRACT

Water or acidified water can be used to extract N-methylpyrrolidone from a mixture containing phenol and N-methylpyrrolidone. In one embodiment of this invention water or acidified water can be used to extract N-methylpyrrolidone from the kettle bottoms of the N-methylpyrrolidone recovery column of a poly(phenylene sulfide) polymerization process.

11 Claims, No Drawings

EXTRACTION OF N-METHYLPYRROLIDONE-2

This invention relates to the extraction of N-methylpyrrolidone from a mixture containing phenol and N-methylpyrrolidone. An embodiment of this invention relates to the treatment of the kettle bottoms of an N-methylpyrrolidone recovery distillation column with water or acidified water to extract N-methylpyrrolidone.

BACKGROUND

The preparation of poly(phenylene sulfide) can be accomplished by heating p-dichlorobenzene in the presence of a partially dehydrated mixture of sodium sulfide and N-methylpyrrolidone as disclosed in U.S. Pat. No. 3,354,129. U.S. Pat. No. 3,354,129 is incorporated by reference into this disclosure. After completion of the polymerization reaction, the poly(phenylene sulfide) can be recovered by flash evaporation of the volatile components, i.e., N-methylpyrrolidone, water, unreacted p-dichlorobenzene and volatile by-products of the polymerization reaction. U.S. Pat. Nos. 4,056,515 and 4,060,520 teach such a process and are incorporated by reference into this disclosure. A significant volatile by-product of the polymerization reaction is phenol. Other by-products include diphenyl ether and N-methyl-succinimide.

In order to recover N-methylpyrrolidone the flashed volatiles are fractionated in two successive distillation processes. The flashed volatiles are first passed to a "lights column" where water, unreacted p-dichlorobenzene and the more volatile by-products are removed overhead. The less volatile by-products (including phenol, diphenyl ether and N-methyl-succinimide) and N-methylpyrrolidone accumulate at the bottom of the "lights column." These kettle bottoms are subsequently fed into an "N-methylpyrrolidone recovery column" which generally operates at a temperature higher than that of the first column.

The overhead of the second recovery column is relatively pure N-methylpyrrolidone. Phenol, an impurity, accumulates at the bottom of the column so long as the phenol concentration in the kettle bottoms remains low (generally less than about 20 weight percent) and the temperature of the kettle bottoms remains low (generally below about 460° F.). Above these levels the phenol codistills with N-methylpyrrolidone. Because N-methylpyrrolidone is recycled to the polymerization step and because phenol adversely affects polymerization, codistillation of the phenol is highly undesirable.

It is well known that N-methylpyrrolidone (also called N-methyl-$\gamma$-butyrolactam) and phenol form a 1:1 adduct as disclosed in the Journal of Organic Chemistry 29, 3122–3124 (1964) incorporated by reference herein. This adduct formation apparently explains why phenol accumulates in the kettle bottoms even though it has a lower boiling point than N-methylpyrrolidone. Under the distillation conditions of the "N-methylpyrrolidone recovery column" a considerable excess of N-methylpyrrolidone relative to the amount of phenol must be present in the column in order to preserve the thermal stability of the adduct. For this reason, a significant amount of N-methylpyrrolidone (about four times the amount of phenol) cannot be recovered by distillation since it must remain in the kettle bottom to bind phenol and thus prevent the phenol from distilling overhead and contaminating the N-methylpyrrolidone. This incomplete recovery is costly in that a valuable reagent is lost and kettle bottom disposal problems are magnified.

SUMMARY OF THE INVENTION

In brief summary, this invention resides in the use of water or acidified water to extract N-methylpyrrolidone from a mixture containing phenol and N-methylpyrrolidone such as the above-described kettle bottoms.

OBJECTS OF THE INVENTION

Accordingly it is an object of this invention to extract N-methylpyrrolidone from the kettle bottoms of an "N-methylpyrrolidone recovery column."

More generally it is an object of this invention to extract N-methylpyrrolidone from a mixture containing phenol and N-methylpyrrolidone.

These objects and other objects and advantages of the invention will be made apparent from a study of this disclosure and the appended claims.

DETAILED DESCRIPTION OF THE INVENTION

I have discovered a method whereby a substantial portion of the N-methylpyrrolidone content of the kettle bottoms of an "N-methylpyrrolidone recovery column" can be recovered by extraction with water or acidified water. As compared to phenol and the other by-products or impurities, a disproportionately larger percentage of N-methylpyrrolidone is dissolved in the water. In other words, after extraction, comparison of the resultant aqueous phase to the resultant organic (or oil) phase reveals that the weight percentage ratio of N-methylpyrrolidone to phenol and other impurities is greater in the aqueous phase than in the organic (or oil) phase. Separation of water and N-methylpyrrolidone can be accomplished by fractional distillation in the "lights column" or by extraction with a suitable organic material not miscible with water.

The scope of this invention is not limited to application in a poly(phenylene sulfide) process but includes the extraction of N-methylpyrrolidone from any mixture comprising phenol and N-methylpyrrolidone.

By using acidified water, more N-methylpyrrolidone can be extracted per unit of extracted phenol, i.e., the weight percentage ratio of extracted N-methylpyrrolidone to extracted phenol can be increased. The acidified water generally extracts more of the other by-products or impurities and as a result the overall weight percentage of N-methylpyrrolidone in the extracted aqueous phase may be slightly less than with non-acidified water. This, however, may not be an unacceptable price to pay for improving, i.e., increasing, the N-methylpyrrolidone to phenol ratio in the extracted aqueous phase because phenol is the least desirable impurity and is believed to be the most difficult to separate from N-methylpyrrolidone.

If it is desired to use acidified water it is currently preferred to acidify the water with acetic acid because this acid is a weak acid and is readily available. Persons of ordinary skill in the art will easily recognize other suitable acids. Accordingly, the scope of this invention is not limited to any specific acid but rather embraces all acids recognized by those skilled in the art to be useful for the intended purpose.

The invention can be successfully practiced by using conventional liquid-liquid extraction techniques. Since extraction utilizes differences in the solubilities of the components it is desirable that the water and the N- methylpyrrolidone and phenol-containing solution be brought into good contact to permit transfer of material. The extraction may be conducted batchwise or continuously. Examples of suitable extraction equipment include mixer-settlers, spray columns, packed columns, perforated-plate columns, baffle columns, and agitated towers.

The amount of water used will depend upon the extraction technique and equipment employed and upon other constraints and objectives. It is generally contemplated that the weight percentage ratio of water to N-methylpyrrolidone will range from about 20:1 to about 1:2 but the scope of this invention is not limited thereby. The presently preferred range is about 8:1 to about 2:1.

Successful practice of the invention is contemplated at, but not limited to, extraction temperatures ranging from about 50° F. to about 250° F. and extraction pressures ranging from about 0 to about 200 psig. Given this disclosure, optimum temperature, pressure and other operational parameters can be determined by a skilled practitioner of the art. The essence of this invention is found in the use of water or acidified water to extract a disproportionately greater percentage of N-methylpyrrolidone from a mixture containing phenol and N-methylpyrrolidone.

The following examples illustrate the practice of my invention and demonstrate its operability.

EXAMPLE I

The experimental runs of this example involve the extraction of the kettle bottoms of an "N-methylpyrrolidone recovery column" with water. The results demonstrate that the weight percentage ratio of extracted N-methylpyrrolidone to extracted by-products or impurities in the aqueous extraction phase is greater than in the kettle bottoms. This is particularly significant with respect to the N-methylpyrrolidone to phenol weight percentage ratio.

A sample of the "N-methylpyrrolidone recovery column" kettle bottoms of the Ryton ® polyphenylene sulfide plant of Phillips Petroleum Company was analyzed employing a Perkin Elmer Sigma 3 gas chromatograph filled with 6% K20M (Carbowax poly(ethylene glycol)) on 35/60 mesh Chromasorb T (See run 1). Subsequently, 100 ml of the oily kettle bottom content was added to various amounts of water. After stirring the system for 15 minutes and allowing it to settle, the aqueous layer was decanted from the oil layer through a filter and also analyzed by a Perkin Elmer Sigma 3 gas chromatograph.

The peak areas obtained by employing a gas chromatography detector not responsive to water were used to calculate the weight percentages of the principal impurities in N-methylpyrrolidone. This data is summarized in Table I. The data clearly show that the weight percentage of N-methylpyrrolidone in the water extract was greater than in the oil phase. Conversely, the weight percentage of phenol and other impurities in the water extract was less than in the oil phase. It therefore follows that the affinity of water for N-methylpyrrolidone is greater than the affinity of water for phenol and the other impurities.

TABLE I

| Run | 1 (Control) | 2 (Invention) | 3 (Invention) | 4 (Invention) | 5 (Invention) |
|---|---|---|---|---|---|
| Amount of added water, ml | 0 | 100 | 200 | 300 | 500 |
| Amount of N—methylpyrrolidone | | | | | |
| in water phase, weight %[(a)] | — | 82.02 | 85.13 | 85.19 | 87.50 |
| in oil phase, weight % | 66.24 | — | — | — | — |
| Amount of Phenol: | | | | | |
| in water phase, weight %[(a)] | — | 13.61 | 12.38 | 12.43 | 9.61 |
| in oil phase, weight % | 16.91 | — | — | — | — |
| Amount of Diphenyl ether: | | | | | |
| in water phase, weight % | — | 0.59 | 0.35 | 0.34 | 0.43 |
| in oil phase, weight % | 1.94 | — | — | — | — |
| Amount of N—Methylsuccinimide: | | | | | |
| in water phase, weight %[(a)] | — | 0.29 | 0.23 | 0.17 | 0.35 |
| in oil phase, weight % | 0.51 | — | — | — | — |
| Amount of Others, mainly Unknowns: | | | | | |
| in water phase, weight %[(a)] | — | 3.49 | 1.91 | 1.87 | 2.11 |
| in oil phase, weight % | 14.40 | — | — | — | — |
| Weight % ratio of N—methylpyrrolidone to phenol | 3.92 | 6.03 | 6.88 | 6.85 | 9.11 |
| Weight % ratio of N—methylpyrrolidone to all impurities (including phenol) | 1.96 | 4.56 | 5.72 | 5.75 | 7.00 |

[(a)]determined on a water-free basis, i.e., as weight percentage of solutes in water

EXAMPLE II

Runs 6 and 7 of this example relate to the extraction of N-methylpyrrolidone from the kettle bottom content of an "N-methylpyrrolidone recovery column" with acidified water. In both cases acetic acid was added to the aqueous extractant. Extraction and analysis procedures were the same as in Example I.

The data in Table II indicate that although slightly less N-methylpyrrolidone, on a weight percentage basis, was extracted in runs 6 and 7 (acidified water) than in run 5 (non-acidified water) the N-methylpyrrolidone to phenol weight percentage ratio was improved (i.e., increased) in the latter runs. Because phenol is the most difficult impurity to separate from N-methylpyrrolidone, especially in a subsequent fractionation step, the acid serves a useful purpose.

TABLE II

| Run | 1 (Control) | 5 (Invention) | 6 (Invention) | 7 (Invention) |
|---|---|---|---|---|
| Amount of added water, ml | 0 | 500 | 500 | 500 |
| Amount of acetic acid in water, ml | — | 0 | 5 | 10 |
| Amount of N—methylpyrrolidone | | | | |
| in water phase, weight %[a] | — | 87.50 | 87.43 | 87.13 |
| in oil phase, weight % | 66.24 | — | — | — |
| Amount of Phenol: | | | | |
| in water phase, weight %[a] | — | 9.61 | 8.82 | 8.96 |
| in oil phase, weight % | 16.91 | — | — | — |
| Amount of Diphenyl ether: | | | | |
| in water phase, weight %[a] | — | 0.43 | 0.50 | 0.52 |
| in oil phase, weight % | 1.94 | — | — | — |
| Amount of N—Methylsuccinimide: | | | | |
| in water phase, weight %[a] | — | 0.35 | 0.30 | 0.30 |
| in oil phase, weight % | 0.51 | — | — | — |
| Amount of Others, mainly unknowns: | | | | |
| in water phase, weight %[a] | — | 2.11 | 2.95 | 3.09 |
| in the oil phase, weight % | 14.40 | — | — | — |
| Weight % ratio of N—methylpyrrolidone to phenol | 3.92 | 9.11 | 9.91 | 9.72 |
| Weight % ratio of N—methylpyrrolidone to all impurities (including phenol) | 1.96 | 7.00 | 6.96 | 6.77 |

[a]determined on a water-free basis, i.e., as weight percentage of solutes in water The examples have been given to illustrate the practice of my invention and should not be interpreted to limit its scope.

Reasonable variation from and modification of my invention as herein disclosed and not departing from the essence thereof are contemplated to be within the scope of patent protection desired and sought.

I claim:

1. A method comprising extracting, with water, N-methylpyrrolidone from a mixture comprising N-methylpyrrolidone and phenol; wherein the weight percentage ratio of water added to said mixture to N-methylpyrrolidone originally present in said mixture ranges from 20:1 to 1:2.

2. A method comprising contacting a mixture comprising phenol and N-methylpyrrolidone with water to produce an aqueous phase and an organic phase wherein the ratio of the weight percentage of N-methylpyrrolidone in said aqueous phase to the weight percentage of phenol in said aqueous phase is greater than the ratio of the weight percentage of N-methylpyrrolidone in said organic phase to the weight percentage of phenol in said organic phase and wherein the weight percentage ratio of water added to said mixture to N-methylpyrrolidone originally present in said mixture ranges from 20:1 to 1:2.

3. A method for the recovery of N-methylpyrrolidone from distillation column kettle bottoms in accordance with claim 1 or 2 comprising extraction of said N-methylpyrrolidone from said kettle bottoms with water; wherein said kettle bottoms comprise N-methylpyrrolidone and phenol.

4. A method in accordance with claim 3 wherein said kettle bottoms further comprise diphenyl ether and N-methylsuccinimide.

5. A method in accordance with claim 3 wherein said kettle bottoms are the kettle bottoms of an N-methylpyrrolidone recovery distillation column.

6. A method in accordance with claim 5 wherein said N-methylpyrrolidone has been used in a poly(phenylene sulfide) polymerization process prior to extraction.

7. A method in accordance with claim 3 wherein said water is acidified water.

8. A method in accordance with claim 7 wherein said water has been acidified by the addition of acetic acid.

9. A method in accordance with claim 1 wherein the weight percentage ratio of water to N-methylpyrrolidone ranges from 8:1 to 2:1.

10. A method in accordance with claim 2 wherein the weight percentage ratio of water to N-methylpyrrolidone ranges from 8:1 to 2:1.

11. A method in accordance with claim 3 wherein the weight percentage ratio of water to N-methylpyrrolidone ranges from 8:1 to 2:1.

* * * * *